US009969704B2

(12) United States Patent
Stensrud et al.

(10) Patent No.: US 9,969,704 B2
(45) Date of Patent: May 15, 2018

(54) PHOSPHONIC ACID CATALYST IN DEHYDRATIVE CYCLIZATION OF 5 AND 6 CARBON POLYOLS WITH IMPROVED COLOR AND PRODUCT ACCOUNTABILITY

(71) Applicant: ARCHER DANIELS MIDLAND COMPANY, Decatur, IL (US)

(72) Inventors: Kenneth Stensrud, Decatur, IL (US); Erik Hagberg, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days. days.

(21) Appl. No.: 15/302,368

(22) PCT Filed: Nov. 19, 2014

(86) PCT No.: PCT/US2014/066298
§ 371 (c)(1),
(2) Date: Oct. 6, 2016

(87) PCT Pub. No.: WO2015/156839
PCT Pub. Date: Oct. 15, 2015

(65) Prior Publication Data
US 2017/0015676 A1    Jan. 19, 2017

(30) Foreign Application Priority Data
Apr. 10, 2014 (WO) ................ PCT/US2014/033580

(51) Int. Cl.
*C07D 307/12* (2006.01)
*C07D 307/20* (2006.01)
*C07D 493/04* (2006.01)
*B01J 23/72* (2006.01)
*C07C 29/60* (2006.01)
*C07C 29/132* (2006.01)
*C07G 3/00* (2006.01)
*A23L 27/30* (2016.01)
*B01J 25/00* (2006.01)

(52) U.S. Cl.
CPC ............ *C07D 307/12* (2013.01); *A23L 27/34* (2016.08); *B01J 23/72* (2013.01); *B01J 25/00* (2013.01); *C07C 29/132* (2013.01); *C07C 29/60* (2013.01); *C07D 307/20* (2013.01); *C07D 493/04* (2013.01); *C07G 3/00* (2013.01); *A23V 2002/00* (2013.01)

(58) Field of Classification Search
CPC .. C07D 307/12; C07D 307/20; C07D 493/04; A23L 27/34; B01J 23/72; B01J 25/10; C07C 29/60; C07C 29/132; C07G 3/10
See application file for complete search history.

(56) References Cited

U.S. PATENT DOCUMENTS

| | | | |
|---|---|---|---|
| 2002/0002291 A1* | 1/2002 | Bhatia | C07D 493/04 549/465 |
| 2007/0173654 A1* | 7/2007 | Holladay | C07D 493/04 549/463 |
| 2013/0338381 A1* | 12/2013 | Kim | C07D 493/04 549/464 |

* cited by examiner

*Primary Examiner* — Timothy R Rozof
(74) *Attorney, Agent, or Firm* — William B. Miller

(57) ABSTRACT

A process for preparing materials derived from sugar alcohols such that the dehydration products exhibit better accountability and improved color to water-clear or near water-white appearance is described. In particular, the process involves employing a reducing Brnsted acid (e.g., phosphonic acid) for the catalysis of sugar alcohols to their corresponding dehydrated-cyclized products.

9 Claims, 10 Drawing Sheets

FIG. 16B. Product from dehydration with 0.5 mol% H₂SO₄, 130°C, 3h

PHOSPHONIC ACID CATALYST IN DEHYDRATIVE CYCLIZATION OF 5 AND 6 CARBON POLYOLS WITH IMPROVED COLOR AND PRODUCT ACCOUNTABILITY

BENEFIT OF PRIORITY

The present application is a national phase application of International Application No. PCT/US2014/066298, filed Nov. 19, 2014, which claims benefit of priority from International Application No. PCT/US2014/033580, filed Apr. 10, 2014, the contents of which are incorporated herein by reference.

FIELD OF INVENTION

The present disclosure relates to bi-functional cyclic compounds and process for their synthesis. In particular, the invention pertains to cyclic compounds derived from a reducing Brønsted acid catalyzed dehydration of 5 and 6 carbon polyols and the process in which the cyclic compounds are prepared.

BACKGROUND

Traditionally, polymers and commodity chemicals have been prepared from petroleum-derived feedstocks. However, as petroleum reservoirs are rapidly depleting and concomitantly becoming more difficult to access, an exigency to develop renewable or "green" alternative materials from biologically-derived resources has been at the vanguard of much current research, particularly in the role of commercially tenable surrogates to conventional, petroleum-derived counterparts, or for generating the same materials as produced from fossil, non-renewable sources.

One of the most abundant kinds of biologically-derived or renewable alternative feedstock for such materials is carbohydrates. Carbohydrates, however, are generally unsuited to current high temperature industrial processes. In contrast to petroleum-based hydrophobic aliphatic or aromatic feedstocks with a low degree of functionalization, carbohydrates such as sugars are complex, multi-functionalized hydrophilic materials. As a consequence, researchers have sought to produce biologically-based chemicals that originate from carbohydrates, but which are less highly functionalized, including more stable bi-functional compounds such as 2,5-furandicarboxylic acid (FDCA), levulinic acid, and 1,4:3,6-dianhydrohexitols.

1,4:3,6-dianhydrohexitols (also referred to herein as isohexides) are derived from renewable resources such as cereal-based polysaccharides and the sugars obtained by hydrolysis thereof. Isohexides are a class of bicyclic furanodiols that are derived from the dehydration of corresponding reduced sugar alcohols, for example, D-sorbitol, D-mannitol, and D-iditol are dehydrated and cyclized to A) isosorbide, B) isomannide, and C) isoidide, respectively, the structures of which are illustrated in Scheme 1.

Scheme 1: Structures of isomannide A, isosorbide B, and isoidide C.

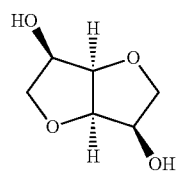
A

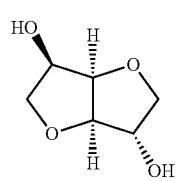
B

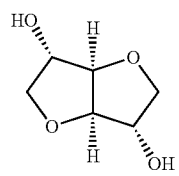
C

The dehydration of sugar alcohols to isohexides by conventional techniques such as use of sulfuric acid typically results in the production of a number of undesirable byproducts. The separation of such byproducts from the desired isohexides as well as other furanic-derivatives remains complicated and costly. Furthermore, the by-products present an undesirable yield loss. Thus, a process that can generate fewer byproducts and higher yields of the desired product, as well as being better in compositional accountability would be welcome.

SUMMARY OF INVENTION

The present disclosure describes, in part, a method for preparing a cyclic derivative product from 5 or 6 carbon polyols. The method involves: reacting a 5 or 6 carbon polyol with a reducing Brønsted acid, alone or in combination with one or more other acid catalyst(s) at a temperature and for a time sufficient to convert the 5 or 6 carbon polyol to a corresponding cyclic intramolecular dehydration product, such that at least 70% or 75% of the sugar alcohol is converted to corresponding cyclic dehydration products. The method may further include purifying the dehydration products by means of at least: chromatography, crystallization, and distillation. The reaction product mixture has an appearance and opacity that ranges from at least translucent, with a medium brown to light honey color, to a transparent, clear or near water-white liquid (i.e., approaching water in colorlessness and clarity) immediately after completion of the reaction, without needing to be subject to a purifying or decolorizing operation. In other words, the reaction product mixture exhibits a color that is lighter and more translucent relative to a reaction product prepared using conventional sulfuric acid catalyst.

In various embodiments the cyclic dehydration products include at least one of 1,4-anhydroglucitol (1,4 sorbitan), 2,5-anhydroglucitol(s) (2,5 sorbitans), 1,4:2,5-anhydromannitol, 1,4-anhydroxylitol, or 1,4:3,6-dianhydrohexitols such as isosorbide, isomannide, isoiodide or 2,5-bis-(hydroxymethyl)-tetrahydrofuran (THE diol). In exemplary embodiments with sorbitol, mannitol or iditol being the 5 or 6 carbon polyol the product mixture includes at least one of isosorbide, isomannide, or isoiodide as a primary product and sorbitans as secondary products. In embodiment where xyilol is the 5 or 6 carbon polyol, the primary reaction product is 1,4-anhydroxylitol. In an embodiment where 1,2,5,6 hexanetetrol is the 5 or 6 carbon sugar polyol, THF-diol is the primary product.

Additional features and advantages of the present methods will be disclosed in the following detailed description.

It is understood that both the foregoing summary and the following detailed description and examples are merely representative of the invention, and are intended to provide an overview for understanding the invention as claimed.

BRIEF DESCRIPTION OF FIGURES

FIGS. 16A and 16 B are photographs of bottles containing a comparative sample product of dehydration with 1 mol % $H_2SO_4$, 110° C., 3 h., (16A), and 0.5 mol % $H_2SO_4$, 130° C., 3 h., (16B), respectively.

DETAILED DESCRIPTION OF INVENTION

I. Description of Invention

Figure 1:
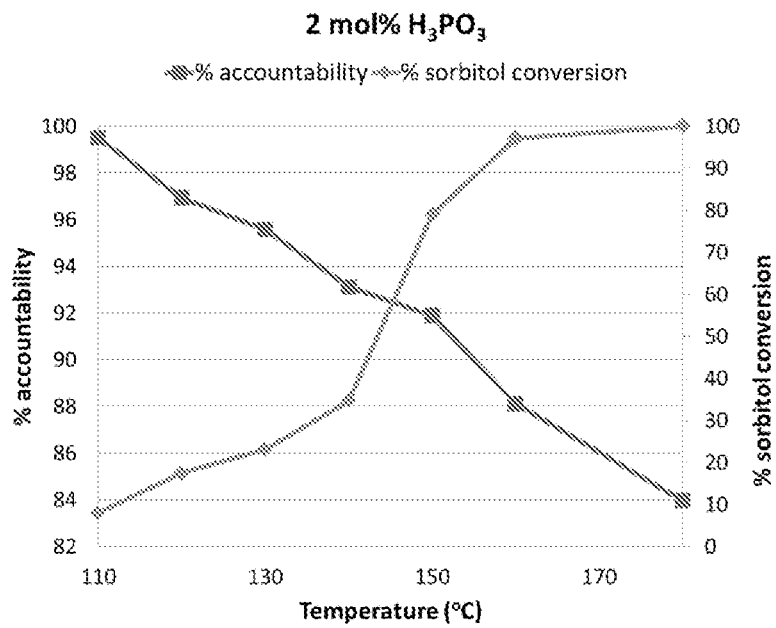
FIG. 1 is a graph showing the relative percentage of sorbitol conversion and percentage of product composition accountability at various reaction temperatures using phosphonic acid ($H_3PO_3$) catalyst (2 mol. % catalyst load).

The present disclosure describes a method that can improve color and increase compositional accountability in product mixtures prepared from dehydration reactions of 5 or 6 carbon polyols. In general, the method involves reacting a 5 or 6 carbon polyol with a reducing Brønsted acid catalyst at a temperature and for a time sufficient to convert the 5 or 6 carbon polyol to a corresponding cyclic intramolecular dehydration product. The acid catalyst has a pKa between about 1 and about 3 (±0.5), at a temperature sufficient to convert substantially all of the 5 or 6 carbon polyol to a corresponding intramolecular dehydration product (e.g., 1,4-anhydroglucitol (also commonly referred to as 1,4 sorbitan), 2,5-anhydroglucitol(s) (also commonly referred to as 2,5 sorbitans), 1,4:2,5-anhydromannitol, 1,4-anhydroxylitol, or 1,4:3,6-dianhydrohexitols). The acid catalyst can be a 1) reducing Brønsted acid, alone or in combination with a 2) Lewis acid, or 3) solid-phase acid catalyst.

In addition to the dehydration product the resultant reaction product mixture may have one or more poly-condensation products. The constituents of the composition of the reaction product mixture is accountable to a level greater than about 70% or about 75%. The reaction product mixture has an opacity and color appearance that ranges from at least translucent, with a medium brown to light honey color, or all the way to a transparent, clear or near water-clear or water-white liquid immediately after completion of the reaction, without having to be subject to a subsequent purifying or decolorizing operation. (See e.g., FIGS. 9, 11, and 12.) In other words, the method is able to yield a cleaner initial product mixture, relative to conventional reaction systems, and which contains more identifiable components and less miscellaneous polymerized by-products.

The methods described herein are exemplified by use of phosphonic acid ($H_3PO_3$) also known as phosphorus acid, to perform the dehydration of 5 or 6 carbon polyols to their corresponding cyclic derivatives. Unlike phosphoric acid ($H_3PO_4$) and other Brønsted acids such as sulfuric acid that have previously been used to dehydrate 5 or 6 carbon polyols, phosphonic acid has a higher pKa of 1.30 and also acts as a reducing agent wherein phosphonic acid is oxidized to phosphoric acid with reduction of another chemical species in a reaction mixture. Hence, phosphonic acid is an example of a reducing Brønsted acid. The reducing potential of such acids allow for their use as both a reducing agent and proton donor. Other examples of reducing acids are organic derivatives of phosphonic acid having the formula $R(H_2PO_3)$ where R is an alkyl or aryl moiety, and sulfonic acid ($H_2SO_3$) and its corresponding organic derivatives.

Although not explored extensively as an acid catalyst, we have found that a reducing Brønsted acid such as phosphonic acid can be used alone or in combination with other Brønsted or Lewis acid catalysts for the conversion of a 5 or 6 carbon polyol to its corresponding cyclic bifunctional derivative material with significant advantages. First, a reaction catalyzed with a reducing Brønsted acid can reduce significantly the formation of unwanted color bodies that cause the typical dark coloration of product mixtures made from reactions that employ conventional or ordinary Brønsted acid catalysts such as sulfuric acid. Second, a reducing Brønsted acid catalyst can increase product compositional accountability of the reaction (i.e., it can convert more of the 5 or 6 carbon polyol to an indefinable cyclized derivative) while maintaining favorable levels of conversion activity. In operational terms, some specific advantages of $H_3PO_3$ is that it can be introduced to a reaction as a solid which can enable greater control of the reaction, and with a higher pKa (~1) than that of sulfuric acid, the reaction medium does not need to be neutralized with significant quantities of base for subsequent downstream purification steps. The higher $pK_a$ also limits the degree of byproduct formation. Hence, the use of phosphonic acid confers advantages for both reactivity and subsequent purification operations.

These features can lead to manufacturing cost savings by reducing or eliminating the need for often complex and costly downstream operations to purify and/or decolorize the products. Typically, after 5 or 6 carbon polyols are made into their corresponding dehydration products, the product mixture is subjected to a series of post-reaction purification processes. These processes may include, for instance, quenching or neutralization of acids, filtration, ion exchange chromatography, and carbon polishing to remove residual color. Each of these steps can be expensive and time consuming. An advantage of the present catalysts system and reactions described herein is that it can minimize or eliminate one or more of these steps (e.g., neutralization, disposal of salts, cationic chromatography, and carbon polishing to mitigate color). Nonetheless, although not required, the method may further include purifying the dehydration products using, for example, chromatography, crystallization, or distillation, so as to achieve higher quality or purity products.

Another advantageous feature of the present method is a capability to convert from at least 80% to substantially all of the 5 or 6 carbon polyol starting material to the corresponding intramolecular dehydration product, while maintaining a relative concentration of poly-condensation product in the reaction product mixture at a low level, less than 25% of total products. In certain embodiments, the relative concentration of poly-condensation products in the reaction product mixture can be less than about 20% (e.g., desirably under about 15%, 17%, or 18%). The reaction can generate a yield of dehydration product of at least 50%; typically the yield is about 75%-80% or greater. In certain favored embodiment the yield can be in a range between about 85%, 88% or 90%, to about 95%, 98%, or 99%.

As shown qualitatively in the accompanying photographs (e.g., FIGS. 9-15A-C), a reaction performed according to an embodiment of the present invention manifests a lighter color in the samples. The reaction product mixture exhibits a color appearance that is lighter and more translucent relative to a reaction product prepared using conventional acid catalysts, such as sulfuric acid (FIGS. 11, 16A & 16B), at a catalyst load of ≥0.1 mol %, instead of the reducing phosphonic acid catalyst for the same time and temperature. This phenomenon, we believe results from reduced levels of color body formation and accumulation in the product mixture relative to a product mixture prepared using sulfuric acid (e.g., at a catalyst load of ≥0.1 mol. %).

Phosphonic acid catalyst can be employed in the conversion of various different 5 or 6 carbon polyol species to their corresponding products. According to certain embodiments, the 5 or 6 carbon polyol can be, for example, sorbitol, mannitol, iditol, xylitol, and 1,2,5,6-hexanetetrol (HTO). For instance, sorbitol is converted to isosorbide by means of intramolecular dehydrative cyclization of sorbitol to sorbitans, then isosorbide. In another example, xylitol can be dehydrated directly to 1,4-anhydroxylitol. Alternatively, HTO is cyclized dehydratively to racemic THF diol.

Phosphonic acid may be employed at a catalyst load of about 1 mol. % or 2 mol. % to about 15 mol. % or 20 mol. %, relative to the concentration of the 5 or 6 carbon polyol, or any combination of range values therein. In certain other embodiments, the phosphonic acid is at a catalyst load in a range from about 5 mol. % or 7 mol. % to about 10 mol. % or 13 mol. %, relative to a concentration of said 5 or 6 carbon polyol.

The reaction time may be up to about 3 hours, but typically to minimize color body formation the reaction times are shorter between about 1 to 2 hours.

The reaction temperature may be in a range from about 100° C. up to about 180° C. Typically, the reaction temperature is in a range from about 110° C. or 120° C. to about 150° C. or 160° C. To obtain optimal product yields, the dehydration reaction is performed under vacuum at an operating pressure of about 5 torr to about 100 torr. Typically, the operating pressure is between about 10 torr to about 30 torr, preferably between about 12 or 15 torr to about 20 or 25 torr.

1. Compositional Accountability

When a 5 or 6 carbon polyol is dehydrated by an acid catalyst some byproducts are formed that are not readily identifiable, meaning there are products formed that are not identified as a particular cyclic dehydration derivative species (e.g., not an isohexide or sorbitan compound). These difficult to identify byproducts include polymerization condensates and color bodies, both of which impart an unwanted color and opacity to the reaction mixture. "Accountability" as used herein, is a measure of the percentage of the product mixture that can be quantitatively identified as one of the cyclic dehydration derivative compounds and therefore excludes poly-condensates, color bodies or other species (e.g., furanic compounds) that are not identified as a cyclic dehydration product. According to an advantageous feature of the present methods use of phosphonic acid to dehydrate 5 or 6 carbon polyols results in a product mixture with high accountability, especially relative to sulfuric acid catalyzed dehydration.

Figure 2:
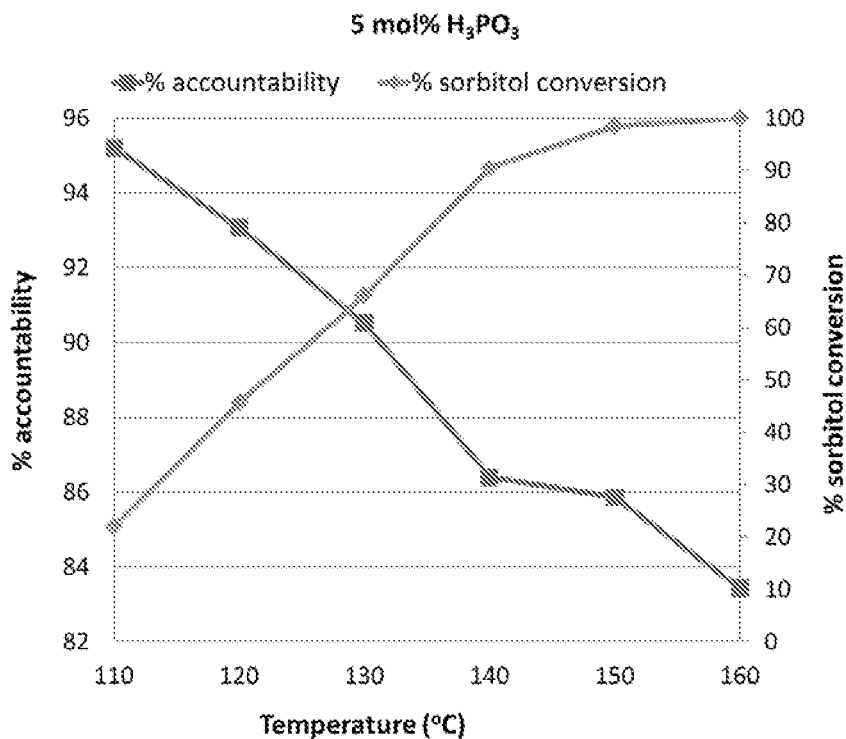
FIG. 2 is a graph showing the relative percentage of sorbitol conversion and percentage of product composition accountability at various reaction temperatures using phosphonic acid catalyst (5 mol. % catalyst load).
Figure 3:
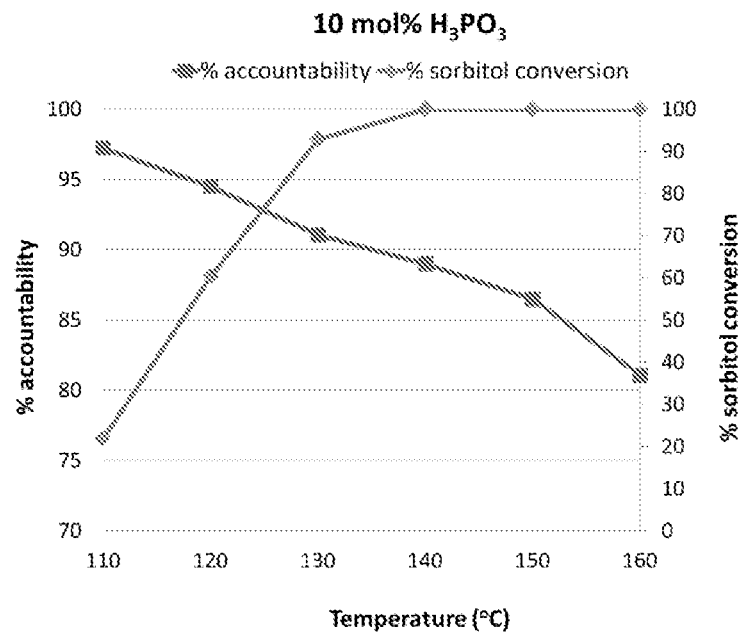
FIG. 3 is graph showing the relative percentage of sorbitol conversion and percentage of product composition accountability at various reaction temperatures using phosphonic acid catalyst (10 mol. % catalyst load).

FIGS. 1-3, show the percentage of sorbitol converted to some reaction product (sorbitol conversion) (right y-axis) and the percentage of those products that are identified as an accountable product (accountability) (left y-axis) at various reaction temperatures (x-axis) using phosphonic acid ($H_3PO_3$) catalyst at various catalyst loading levels. In each case the reaction time was three hours. The respective conversion rate of sorbitol and product accountability is inversely affected by temperature. Higher temperatures lead to higher sorbitol conversion but also to lower product accountability. For example, FIG. 1 shows that for a reaction using 2 mol. % $H_3PO_3$ catalyst at about 110° C. the sorbitol conversion is only about 83% while the product accountability is nearly 100%; however, at a temperature of 160° C.

the conversion amount is nearly 100% but the product accountability drops to about 88%. This overall trend remains regardless of the load rate of catalysts, as shown in FIGS. 2 and 3.

Figure 4:
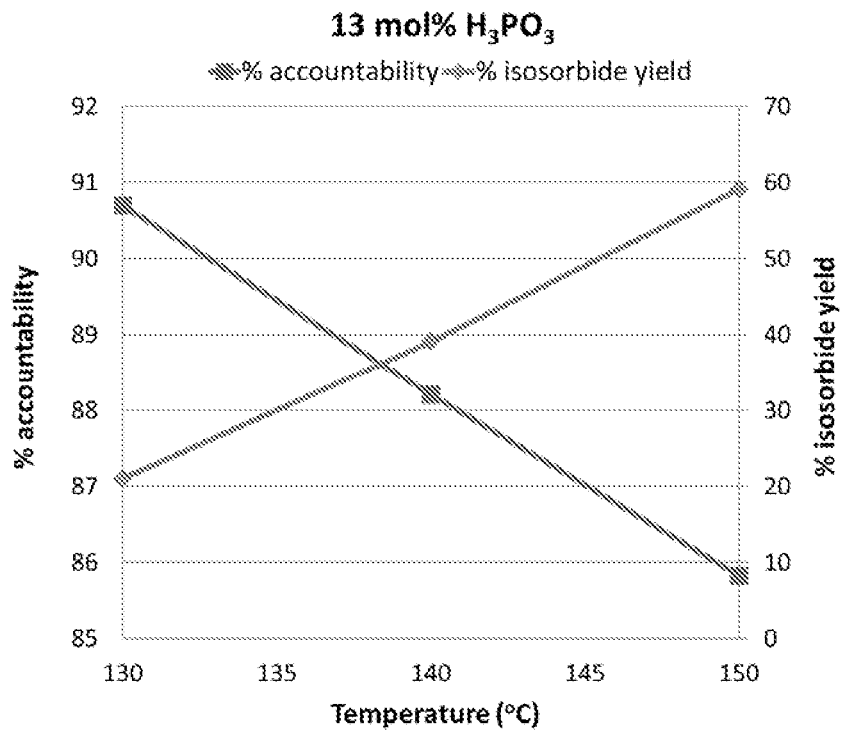
FIG. 4 is a graph showing the relative percentage of isosorbide yield and percentage of product composition accountability at various reaction temperatures using phosphonic acid catalyst (13 mol. % catalyst load).
Figure 5:
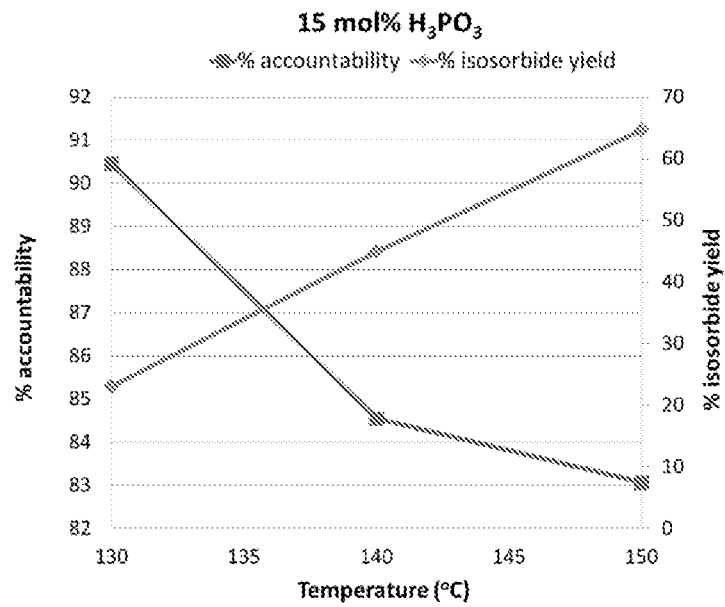
FIG. 5 is a graph showing the relative percentage of isosorbide yield and percentage of product composition accountability at various reaction temperatures using phosphonic acid catalyst (15 mol. % catalyst load).
Figure 6:
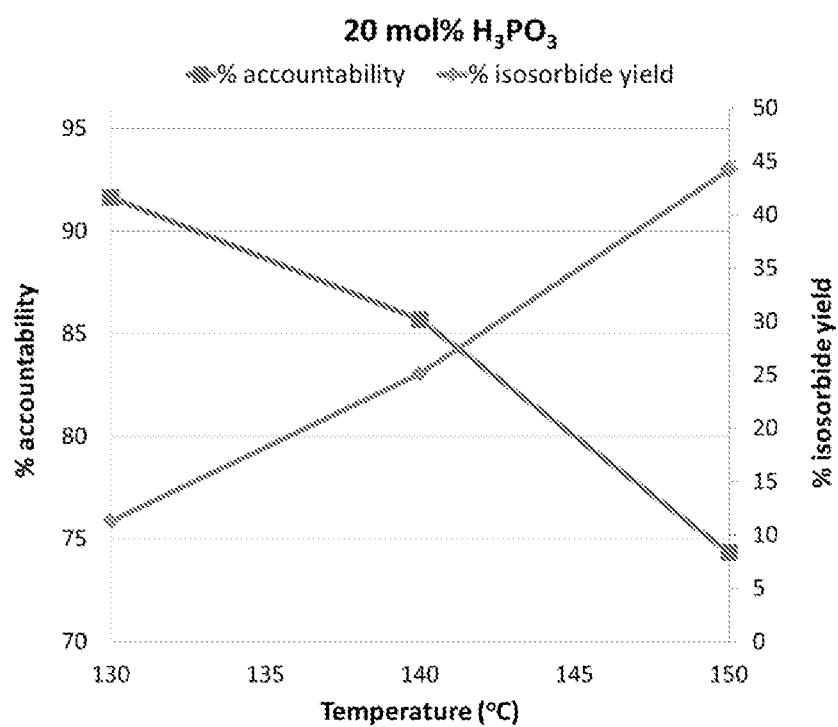
FIG. 6 is a graph showing the relative percentage of isosorbide yield and percentage of product composition accountability at various reaction temperatures using phosphonic acid catalyst (20 mol. % catalyst load).

FIGS. 4, 5, and 6 compare the percentage yield of isosorbide (isosorbide yield) (right y-axis) and the percentage of the product that are identified as an accountable component (accountability) (left y-axis) as various reaction temperatures (x-axis), at phosphonic acid catalyst loadings of 13 mol. %, 15 mol. %, and 29 mol. %, respectively. In each case the reaction time was three hours. Like in FIGS. 1-3, with respect to sorbitol conversion rates and product accountability, the percentage yield of isosorbide and percent product accountability are related inversely. Isosorbide yield tends to increase with rising temperature, while product accountability decreases.

In certain embodiments, the phosphonic acid catalyst is able to maintain about 60% isosorbide yield, while enabling concomitantly near complete sorbitol conversion (>95%). The phosphonic acid catalysis reactions of FIGS. 1-3 manifest 100% sorbitol conversion. These results compare favorably to similar results for the reactions of FIGS. 7 and 8 (>93% sorbitol conversion) from sulfuric acid catalysis.

In aggregate, the data suggests that one can control or modulate time, temperature, and catalyst load to balance and optimize desired target yields, product accountability, and color. Higher catalyst loads facilitates quick conversion of the 5 or 6 carbon polyol to its corresponding dehydration product at relatively low temperatures, but with a loss of accountability.

For example, at relatively low levels of catalyst (e.g., ~2 mol. % in FIG. 1, or ~5 mol. % in FIG. 2), the 5 or 6 carbon polyol conversion rates, while acceptable, may require higher temperatures to help achieve higher conversion rates of more than about 50%-70%, while maintaining good levels of product accountability (≥85%). At medium catalyst levels (e.g., ~10 mol. % in FIG. 3 to ~13 mol. % in FIG. 4 or ~15 mol. % in FIG. 5), one also may need to use a higher temperature and longer reaction times. At high catalyst levels (e.g., ~20 mol. % in FIG. 6), however, a lower temperature or shorter reaction time can help to reduce or minimize color body accretion while maintaining high yield of isosorbide product.

Figure 7:
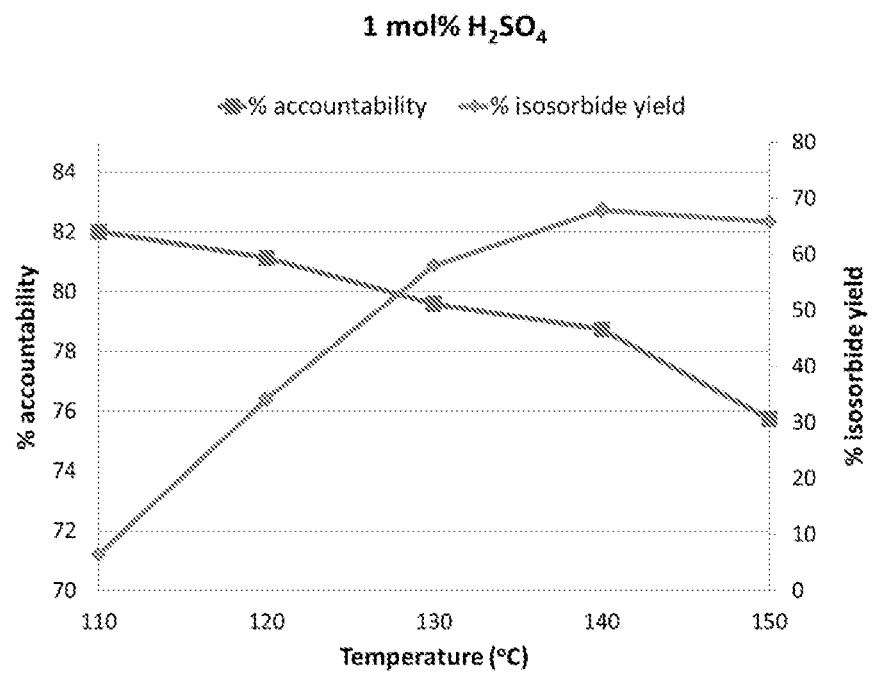
FIGS. 7 and 8 are graphs for comparison showing the relative percentage of sorbitol conversion and percentage of product composition accountability at various reaction temperatures using a conventional catalyst, sulfuric acid ($H_2SO_4$), respectively, at 1.0 mol. % and 0.5 mol. % catalyst load.
Figure 8:
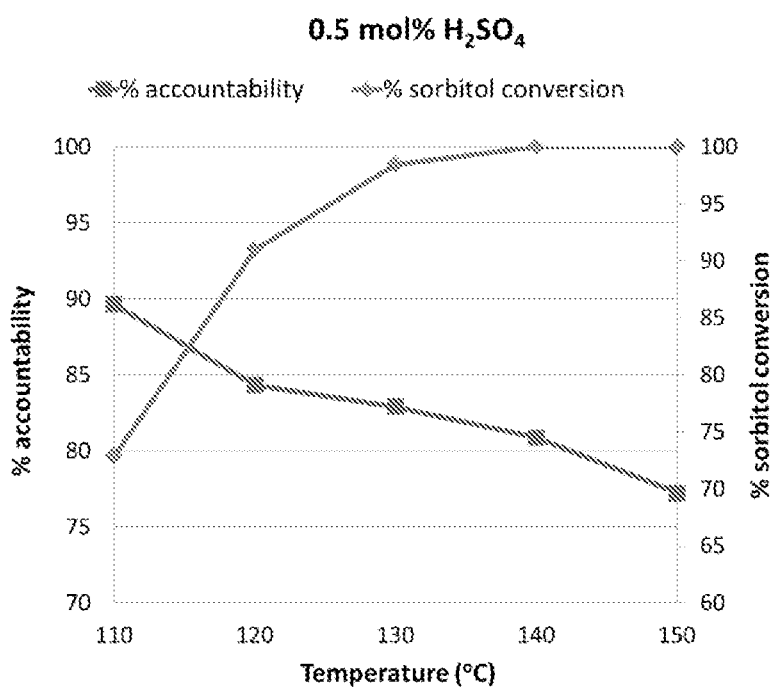

The phosphonic acid catalyst performs functionally at least equivalent to sulfuric acid in terms of product accountability and isosorbide yield, such as presented respectively in a comparison of FIGS. 4 and 7. The conventional sulfuric acid has maximum yield of about 60%-67% for isosorbide, and about 75%-78% product accountability. FIG. 4, shows that a reaction catalyzed at 13 mol. % $H_3PO_3$, 150° C. achieves about a 86% product accountability, which is about a 10% improvement over the 1 mol. % sulfuric acid catalysis, delineated in FIG. 7.

2. Color Mitigation

Figure 9:
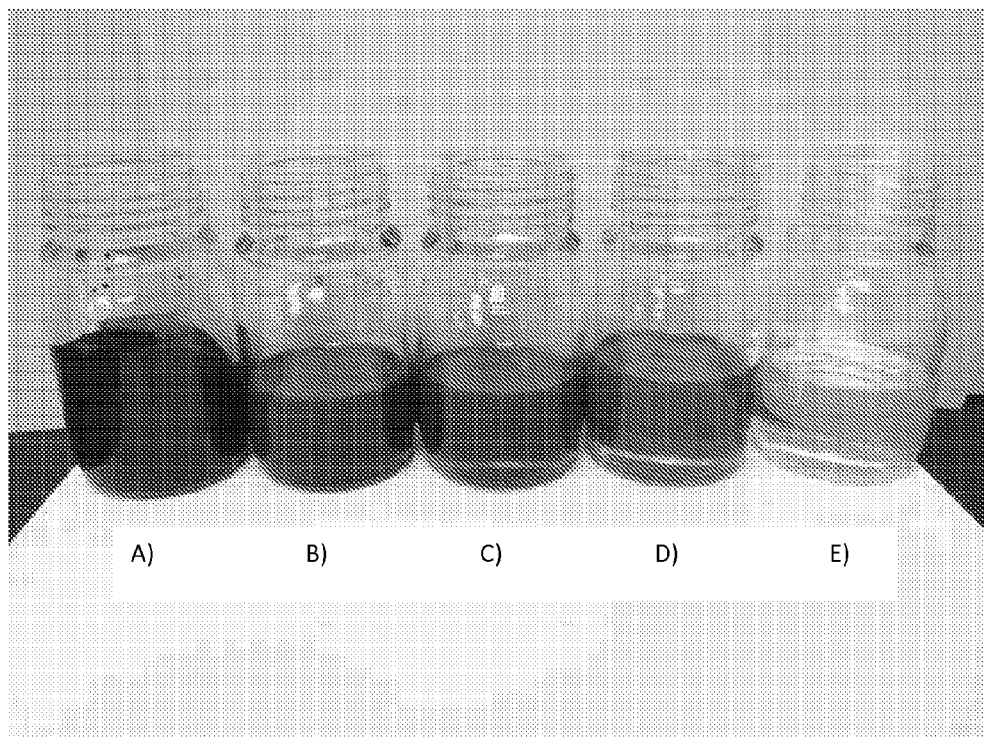
FIG. 9 is a photograph showing jars containing product mixtures from sorbitol dehydration performed using different kinds of acid catalysts, and respective opacity and color appearance for each product mixture, which from left to right, ranges from opaque dark brown-black to translucent honey color to transparent light yellow. As shown from left to right, each sample is a product prepared using: A) conventional sulfuric acid (1 mol. % $H_2SO_4$); B) 0.5 mol. % $H_2SO_4$; C) 20 mol. % $H_3PO_3$; D) 10 mol. % $H_3PO_3$; and E) 5 mol. % $H_3PO_3$, each at 140° C. for 2 h at a pressure of >5 torr.
Figure 10:
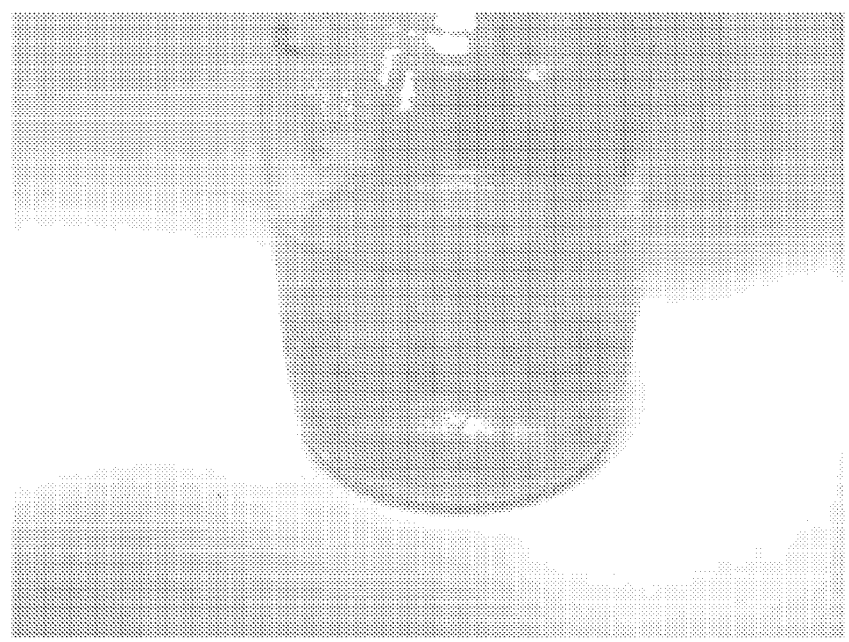
FIG. 10 is a photograph of a vessel containing molten sorbitol feedstock used in the present reactions. As a comparative standard, the sorbitol has mostly transparent white color.

In another aspect, FIG. 9 shows a side-by-side comparison of five dehydration product mixtures prepared at different catalyst loads, respectively, for sulfuric acid (i.e., A) 1 mol. %; B) 0.5 mol. %), and phosphonic acid (i.e., C) 20 mol. %; D) 10 mol. %; and E) 5 mol. %). The appearance of the sulfuric acid catalyzed samples is very dark (black tar-like) in color and opaque. The phosphonic acid catalyzed samples appear as medium to light in color and translucent to transparent. Close-up views of each of the samples are shown in FIGS. 11-16. FIG. 10 showing a vessel containing molten sorbitol feedstock, with a translucent light color, which serves as comparative benchmark.

Table 1, presents a data summary from sorbitol dehydration reactions using phosphonic acid as catalyst at different load levels, run at varied temperatures and times.

TABLE 1

| $H_3PO_3$ Load (mol %) | Time (min) | Temp (° C.) | Sorbitol (wt. %) | Isosorbide (wt. %) | 1,4-sorbitan (wt. %) | 2,5-sorbitan(s) (wt. %) | Accountability (%) |
|---|---|---|---|---|---|---|---|
| 5 | 180 | 130 | 33.16 | 2.91 | 42.61 | 12.81 | 91.49 |
| 5 | 60 | 150 | 24.47 | 5.18 | 49.00 | 15.40 | 94.05 |
| 5 | 120 | 160 | 0 | 35.32 | 35.73 | 17.71 | 88.76 |
| 10 | 120 | 140 | 0 | 12.30 | 58.24 | 17.93 | 88.47 |
| 10 | 60 | 150 | 0 | 16.33 | 57.50 | 15.37 | 89.20 |
| 2.5 | 60 | 150 | 39.65 | 2.51 | 41.68 | 11.57 | 95.41 |
| 2.5 | 120 | 140 | 43.52 | 2.23 | 40.28 | 10.68 | 96.71 |
| 2.5 | 120 | 170 | 0 | 25.92 | 46.83 | 16.53 | 89.28 |
| 2.5 | 180 | 160 | 0 | 26.86 | 46.27 | 16.88 | 90.01 |
| 1 | 180 | 170 | 0 | 21.21 | 46.39 | 20.77 | 90.78 |

Figure 13:
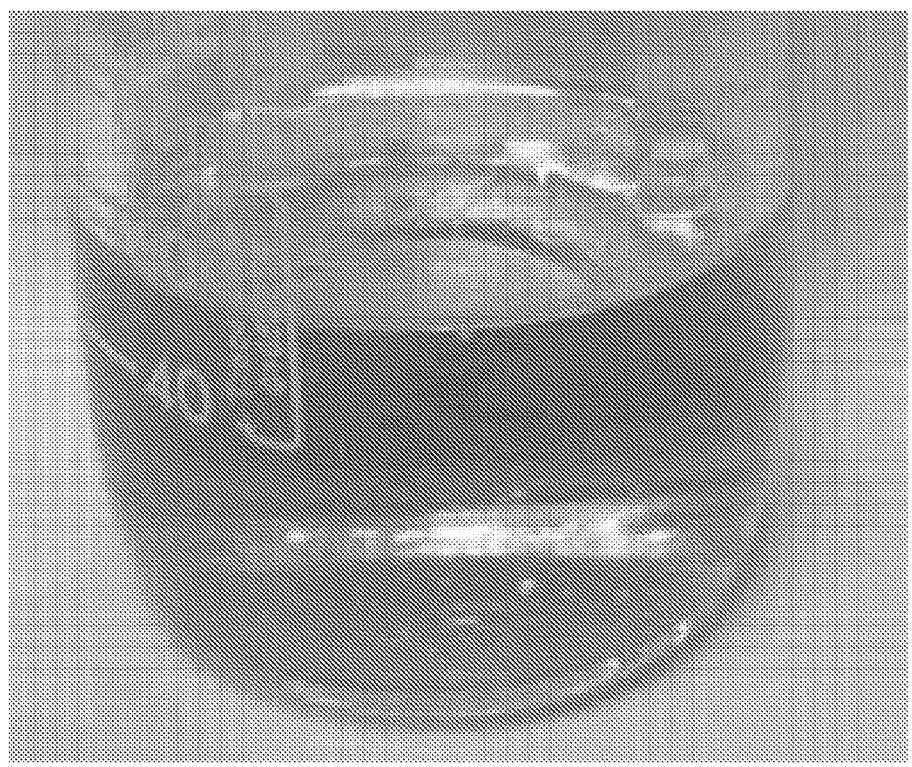
FIG. 13 is a photograph of a bottle containing sample product of dehydration reactions with 10 mol % $H_3PO_3$, 140° C., 3 h.
Figure 14:
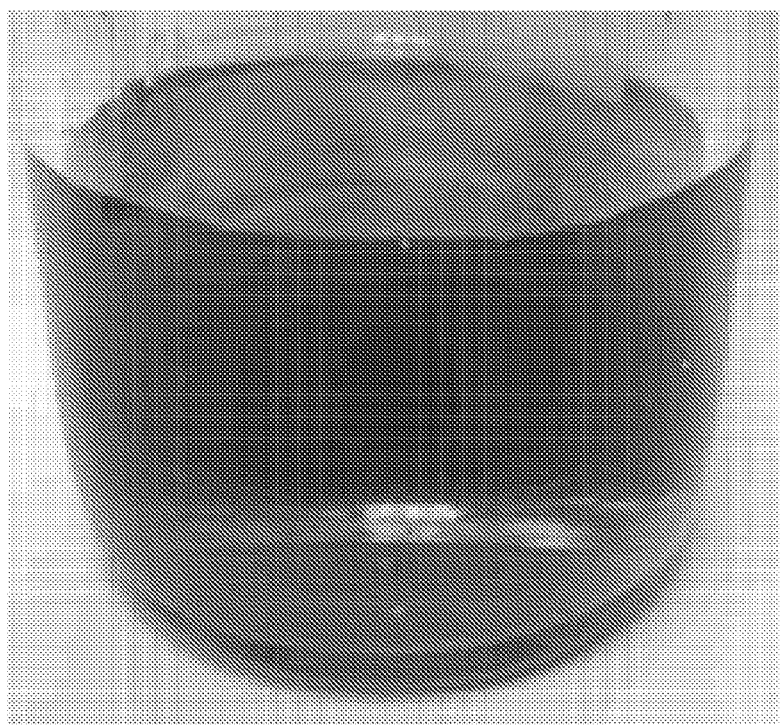
FIG. 14 is a photograph of a bottle containing sample product of dehydration reactions with 10 mol % $H_3PO_3$, 150° C., 3 h.

FIGS. 13-15 are images that show the color mitigation of some of the corresponding samples in Table 1. In FIG. 13 the sample product is from a dehydration reaction using 10 mol. % $H_3PO_3$, 140° C., 3 hours. The color of this sample is a transparent medium yellow. In FIG. 14, the sample product is prepared with 10 mol. % $H_3PO_3$, 150° C., 3 hours. With a higher temperature, the color appears darker because of a higher portion of color bodies in the mixture.

Figure 15A:
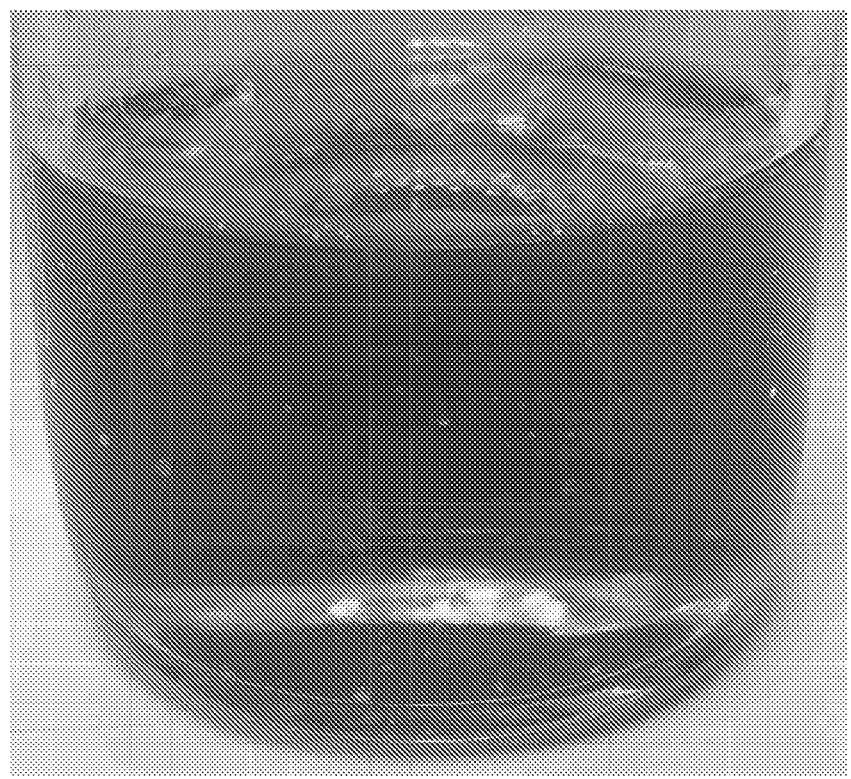
FIGS. 15A, 15B, and 15C are photographs of bottles containing sample product of dehydration with 20 mol % $H_3PO_3$, 140° C., 2 h., (15A), 20 mol % $H_3PO_3$, 150° C., 2 h., (15B), and 10 mol % $H_3PO_3$, 150° C., 3 h., (15C), respectively.
Figure 15B:
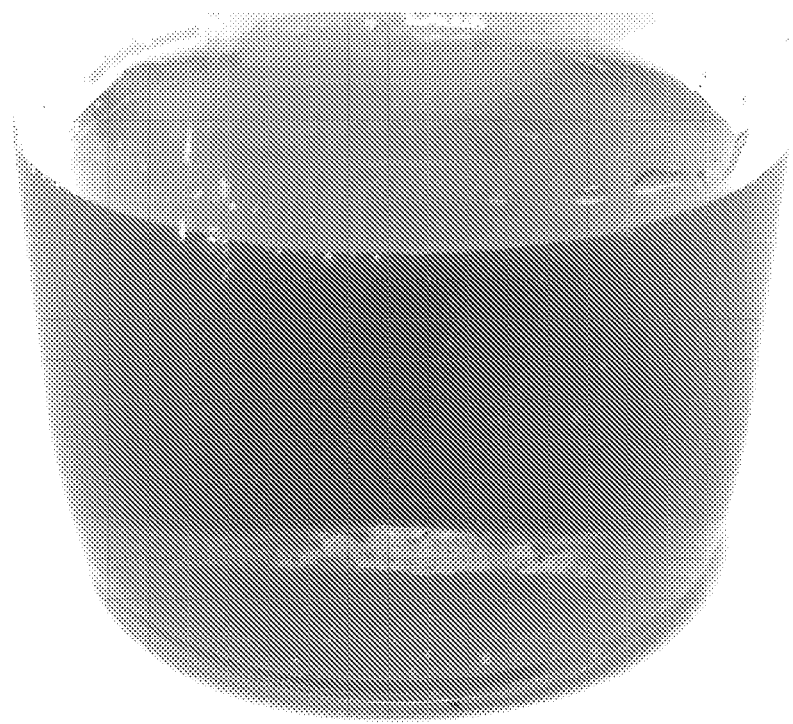
Figure 15C:
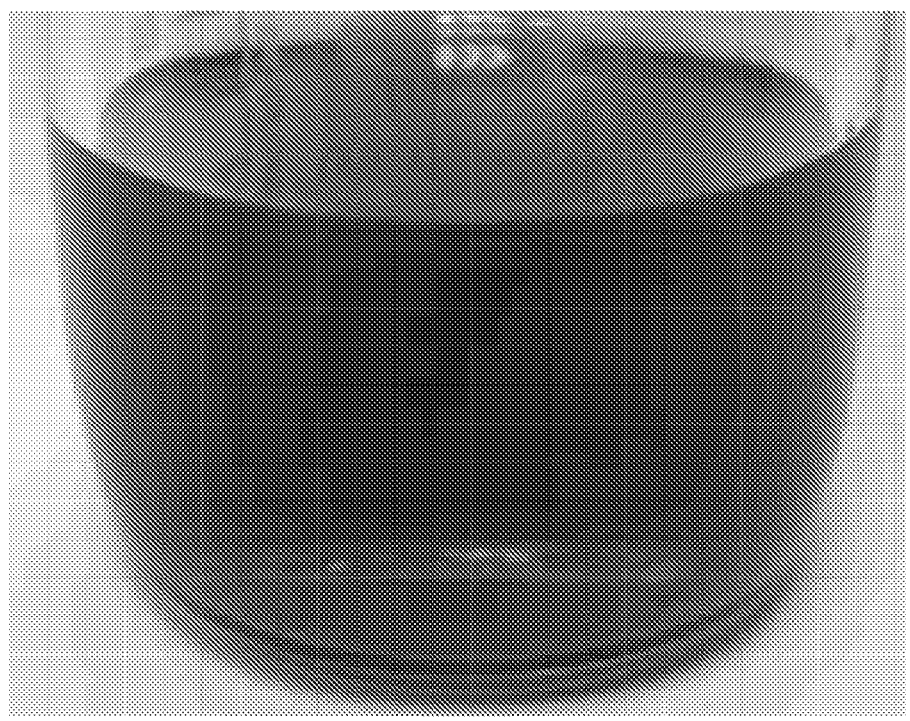
Figure 16A:
Figure 16A:
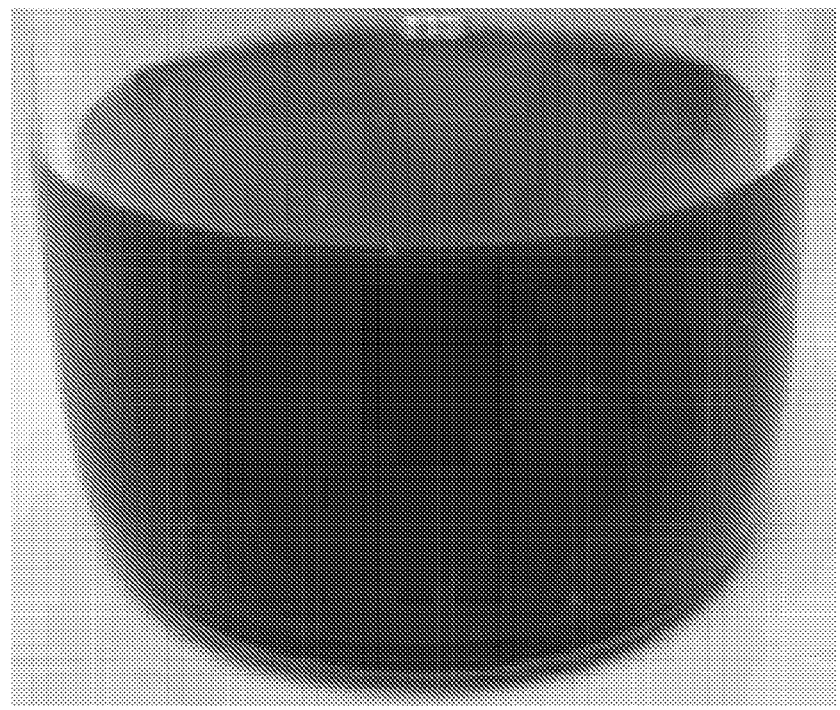

FIGS. 15A, 15B, and 15C are a group of sample dehydration products prepared with 20 mol. % $H_3PO_3$, 140° C., 2 h., (15A), 20 mol. % $H_3PO_3$, 150° C., 2 h., (15B), and 10 mol. % $H_3PO_3$, 150° C., 3 h., (15C), respectively. The series of photos illustrate that even under high catalyst load, high temperatures and extended reaction times, the products have amber to dark honey color, which is significantly better performing than that samples prepared conventionally with sulfuric acid as in FIGS. 16A and 16B, respectively, with 1 mol. % $H_2SO_4$, 110° C., 3 h., (16A), and 0.5 mol. % $H_2SO_4$, 130° C., 3 h., (16B). Even with low catalyst loads and lower temperatures the product mixture is opaque, dark brown to black in appearance. According to certain embodiments, it is believed that about 10 mol. % phosphonic acid is equivalent to about 1 mol. % sulfuric acid in catalytic activity.

3. Sugar Alcohols

A. —Sorbitol

The present method is helpful for the processing of isohexides and the preparation of their dehydration products.

Specifically, the method would be valued for generating sorbitans and isosorbide using a reducing Brønsted acid catalyzed dehydration of sorbitol with accompanying high product accountability and concomitant color body retrenchment.

For purpose of illustration, Table 2 summarizes the results of catalytic dehydration reactions of sorbitol under various reaction conditions according to an embodiment of the present process. In Examples 1-26, the dehydration reactions use phosphonic acid ($H_3PO_3$), at several different catalyst loading levels that range from about 2 mol. % to about 20 mol. %. These reactions are performed at various temperatures between about 110° C. to about 180° C., over a period of about 2 or 3 hours. As the results show, several examples of the phosphonic acid catalysis can produce generally good rates of conversion of sorbitol to isosorbide (e.g., ~65%-100%), which are comparable to reactions that use a strong Brønsted acid, such as sulfuric acid ($H_2SO_4$) as the catalyst, as shown in Comparative Examples 1-10, along with improved composition accountability levels for the product mixture. Phosphonic acid catalyst also out performed a water-tolerant, strong Lewis acid catalyst, such as bismuth triflate ($Bi(OTf)_3$), in terms of product accountability and color attenuation, as presented in Comparative Examples 11-13.

Phosphonic acid exhibits an inherently reductive ability and antioxidant behavior. The unique utility and significant performance characteristics of phosphonic acid as a catalyst, which can generate both good conversion rates and product accountabilities, are shown in Examples 1 and 2 of the section labeled Reducing Acid with Antioxidant. The higher isosorbide yield and color mitigation capacity in the samples highlight the beneficial impact of phosphonic acid as a reducing agent when present at higher acid concentrations.

Examples 3 and 4 compare another antioxidant acid such as ascorbic acid, which has a pKa value close to that of phosphonic acid. The examples show that whereas phosphonic acid can convert completely sorbitol (100%), while generating acceptable amounts of isosorbide, and still maintain about 70% composition accountability, in contrast, the reactions that used ascorbic acid alone did not perform well in regard to these parameters. Even though product accountability levels are high for the ascorbic acid alone samples, this unfortunately is a result of relatively low conversion of sorbitol and virtually no yield of isosorbide.

It is believed that the phosphonic acid functions both as a catalyst for dehydrative cyclization and as reducing agent to help mitigate color development in the product. From the examples and results in the accompanying figures, a favored range for operating conditions of the dehydrative reactions may include phosphonic acid with a concentration of about 2 mol % or 5 mol % to about 10 mol % or 20 mol %, depending on the reaction time and temperature. Longer durations and higher temperatures should be balanced for optimal reaction results.

Certain parameters are discernable from the illustrative examples in Table 2. Generally, higher concentrations (i.e., 15-20 mol. %) of phosphonic acid perform better for sorbitol conversion, product accountability, and color mitigation at low temperatures (e.g., 110-120° C.), and intermediate reaction times (e.g., ~2-3 h). At low concentrations (e.g., ≤5%) of phosphonic acid higher reactions temperatures (e.g., >130° C.) may be needed and/or extended reaction times (>2 h) to fulfill adequate sorbitol conversions, though product accountability is improved and color body retrenchment is generally concurrent. At intermediate concentrations (e.g., 6 mol. %-10 mol. %-13 mol. %) of phosphonic acid, sorbitol conversion can be pronounced at higher temperatures (e.g., 140° C.-150° C.), though reaction times are shortened to maximize product accountability and mitigate color-body accretion. At short reaction times (<2 h) the reaction does not readily promote high sorbitol conversions, but color-body formation is negligible. At moderate to high temperatures (e.g., ~130° C.-150° C.), reaction times are reduced so as to circumvent drops in product compositional accountability and/or color body aggregation.

Certain examples with different combinations of catalyst load, temperature, and time exhibited particularly advantageous results. This suggests potential improvements in combined acid systems.

TABLE 2

Summary of catalytic dehydration reactions of sorbitol under various conditions

| | Catalyst | Load (mol %) | Time (min) | Temp (° C.) | Sorbitol conversion (wt. %) | Isosorbide (wt. %) | 1,4-sorbitan (wt. %) | 2,5-sorbitan(s) (wt. %) | Accountability (%) |
|---|---|---|---|---|---|---|---|---|---|
| Reducing Brønsted Acid, Moderate Strength Example | | | | | | | | | |
| 1 | $H_3PO_3$ | 2 | 180 | 110 | 8.04 | 0.00 | 6.66 | 0.88 | 99.50 |
| 2 | $H_3PO_3$ | 2 | 180 | 120 | 17.49 | 0.00 | 12.08 | 2.34 | 96.93 |
| 3 | $H_3PO_3$ | 2 | 180 | 130 | 23.19 | 0.00 | 14.76 | 4.01 | 95.58 |
| 4 | $H_3PO_3$ | 2 | 180 | 140 | 34.68 | 0.91 | 24.68 | 2.22 | 93.13 |
| 5 | $H_3PO_3$ | 2 | 180 | 150 | 79.02 | 8.04 | 55.82 | 7.05 | 91.89 |
| 6 | $H_3PO_3$ | 2 | 180 | 160 | 97.15 | 15.92 | 56.71 | 11.64 | 88.12 |
| 7 | $H_3PO_3$ | 2 | 180 | 180 | 100.00 | 24.43 | 47.62 | 10.92 | 83.97 |
| 8 | $H_3PO_3$ | 5 | 120 | 140 | 79.19 | 9.76 | 52.10 | 7.05 | 89.72 |
| 9 | $H_3PO_3$ | 5 | 120 | 160 | 98.53 | 19.63 | 52.99 | 10.36 | 86.95 |
| 10 | $H_3PO_3$ | 5 | 180 | 110 | 22.06 | 0.00 | 15.04 | 2.22 | 95.20 |
| 11 | $H_3PO_3$ | 5 | 180 | 120 | 45.72 | 0.77 | 33.09 | 4.93 | 93.07 |
| 12 | $H_3PO_3$ | 5 | 180 | 130 | 66.07 | 3.75 | 44.91 | 7.93 | 90.52 |
| 13 | $H_3PO_3$ | 5 | 180 | 140 | 90.54 | 10.55 | 55.69 | 10.70 | 86.40 |
| 14 | $H_3PO_3$ | 5 | 180 | 150 | 98.49 | 21.04 | 51.38 | 11.93 | 85.86 |
| 15 | $H_3PO_3$ | 5 | 180 | 160 | 100.00 | 29.93 | 42.09 | 8.92 | 83.44 |
| 16 | $H_3PO_3$ | 10 | 180 | 110 | 21.92 | 0.00 | 14.84 | 4.33 | 97.25 |
| 17 | $H_3PO_3$ | 10 | 180 | 120 | 60.33 | 1.71 | 45.62 | 7.49 | 94.49 |
| 18 | $H_3PO_3$ | 10 | 180 | 130 | 92.84 | 16.65 | 52.24 | 10.01 | 91.06 |

TABLE 2-continued

Summary of catalytic dehydration reactions of sorbitol under various conditions

|  | Catalyst | Load (mol %) | Time (min) | Temp (° C.) | Sorbitol conversion (wt. %) | Isosorbide (wt. %) | 1,4-sorbitan (wt. %) | 2,5-sorbitan(s) (wt. %) | Accountability (%) |
|---|---|---|---|---|---|---|---|---|---|
| 19 | $H_3PO_3$ | 10 | 180 | 140 | 100.00 | 31.22 | 41.84 | 10.93 | 88.99 |
| 20 | $H_3PO_3$ | 10 | 180 | 150 | 100.00 | 50.92 | 23.64 | 11.92 | 86.48 |
| 21 | $H_3PO_3$ | 10 | 180 | 160 | 100.00 | 59.01 | 10.67 | 11.39 | 81.07 |
| 22 | $H_3PO_3$ | 13 | 180 | 130 | 96.47 | 20.99 | 48.05 | 10.13 | 90.70 |
| 23 | $H_3PO_3$ | 15 | 180 | 130 | 100.00 | 23.07 | 49.12 | 10.76 | 90.45 |
| 24 | $H_3PO_3$ | 20 | 180 | 130 | 100.00 | 31.18 | 40.09 | 9.65 | 88.42 |
| 25 | $H_3PO_3$ | 20 | 120 | 140 | 100.00 | 25.13 | 32.19 | 11.25 | 85.69 |
| 26 | $H_3PO_3$ | 20 | 120 | 150 | 100.00 | 44.25 | 3.40 | 7.40 | 74.35 |
| Comparative, Strong Brønsted Acid Example | | | | | | | | | |
| 1 | $H_2SO_4$ | 1 | 180 | 110 | 92.28 | 6.46 | 56.99 | 10.84 | 82.01 |
| 2 | $H_2SO_4$ | 1 | 180 | 120 | 99.04 | 34.25 | 36.64 | 9.28 | 81.13 |
| 3 | $H_2SO_4$ | 1 | 180 | 130 | 100.00 | 58.01 | 10.49 | 11.09 | 79.59 |
| 4 | $H_2SO_4$ | 1 | 180 | 140 | 100.00 | 67.92 | 0.00 | 10.82 | 78.74 |
| 5 | $H_2SO_4$ | 1 | 180 | 150 | 100.00 | 65.77 | 0.00 | 9.98 | 75.75 |
| 6 | $H_2SO_4$ | 0.5 | 180 | 110 | 72.87 | 4.66 | 51.99 | 5.84 | 89.62 |
| 7 | $H_2SO_4$ | 0.5 | 180 | 120 | 91.01 | 11.84 | 55.61 | 7.90 | 84.34 |
| 8 | $H_2SO_4$ | 0.5 | 180 | 130 | 98.44 | 27.82 | 43.68 | 9.84 | 82.90 |
| 9 | $H_2SO_4$ | 0.5 | 180 | 140 | 100.00 | 49.09 | 20.80 | 10.98 | 80.87 |
| 10 | $H_2SO_4$ | 0.5 | 180 | 150 | 100.00 | 60.59 | 4.09 | 12.55 | 77.23 |
| Comparative, Water-Tolerant Lewis Acid Example | | | | | | | | | |
| 11 | $Bi(OTf)_3$ | $1.5e^{-5}$ (0.01 wt. %) | 180 | 130 | 17.08 | 0.00 | 5.03 | 0.00 | 98.92 |
| 12 | $Bi(OTf)_3$ | $1.5e^{-5}$ (0.01 wt. %) | 180 | 150 | 49.32 | 1.29 | 36.00 | 7.13 | 95.16 |
| 13 | $Bi(OTf)_3$ | $1.5e^{-4}$ (0.1 wt. %) | 180 | 130 | 53.43 | 1.22 | 36.08 | 6.06 | 96.10 |
| Reducing Acid with Antioxidant Example | | | | | | | | | |
| 1 | $H_3PO_3$* | 10 | 180 | 140 | 100.00 | 24.45 | 33.34 | 9.16 | 70.97 |
| 2 | $H_3PO_3$* | 10 | 180 | 150 | 100.00 | 48.23 | 9.44 | 9.02 | 70.70 |
| Comparative, Antioxidant Alone Example | | | | | | | | | |
| 3 | Ascorbic acid | 5 | 180 | 160 | 33.02 | 0.26 | 16.92 | 3.90 | 92.87 |
| 4 | Ascorbic acid | 2 | 180 | 160 | 15.44 | 0.00 | 10.41 | 2.83 | 99.86 |

*With 1000 ppm ascorbic acid

B.—Mannitol

In another embodiment, phosphonic acid catalyst can likewise contribute to dehydration reactions for the preparation of isomannide from mannitol, congruent with the beneficial results from phosphonic acid catalyzed reactions making isosorbide (i.e., improved accountability and color body retrenchment). Under current processes for making isomannide, the dehydrative cyclization reaction is conducted at least 170° C., the melting temperature of the precursor mannitol. The conventional synthesis process uses strong acid (e.g., sulfuric, sulfonic acid, Lewis acids) catalysts produce exiguous yields of isomannide with concomitant generation of prodigious amounts of polymers or byproducts. When phosphonic acid is applied to isomannide synthesis according to the present invention, the catalytic activity of phosphonic acid is sufficiently strong to effect dehydrative cyclization, but sufficiently weak to prevent polymerization and subsequent production of significant amounts of polycondensates.

Further, phosphonic acid exhibits significantly elevated yields of isomannide and overall product accountability. Scheme 2 outlines the acid-catalyzed dehydrative cyclization of mannitol to isomannide using the common Brønsted acid, $H_2SO_4$, and according to the present reducing Brønsted acid, $H_3PO_3$.

Scheme 2.

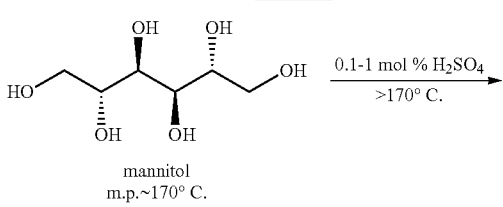

mannitol
m.p. ~170° C.

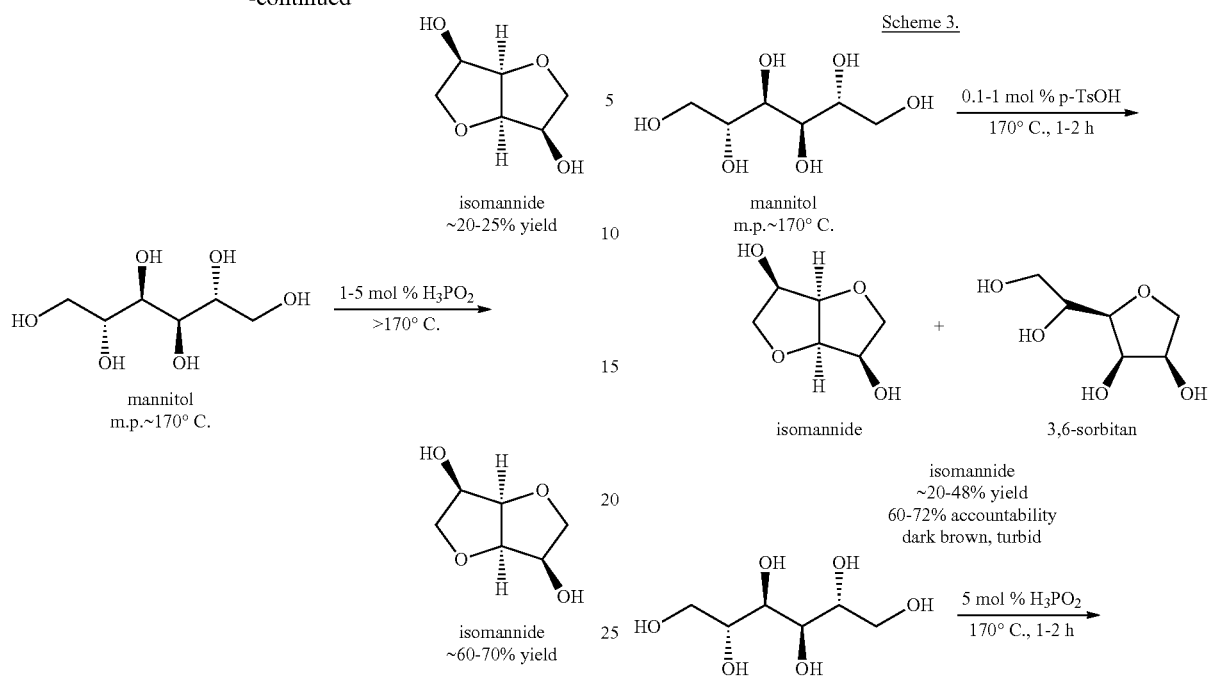
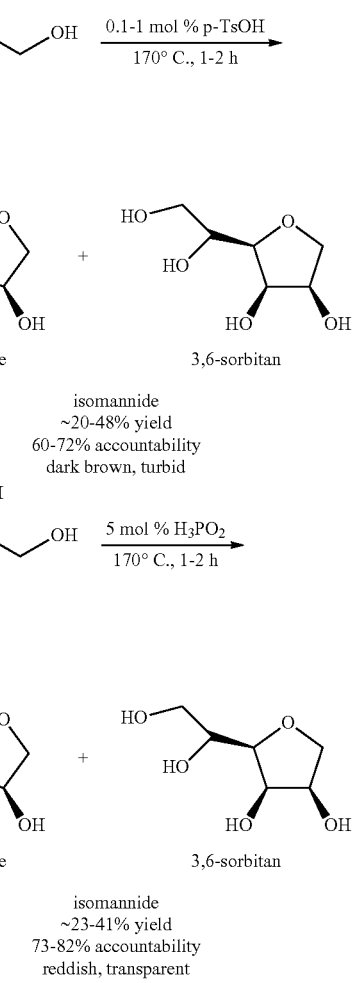

Under similar operation conditions, the percent yield of isomannide achieved from the phosphonic acid catalysis (~60-70%) is significantly greater (~2×-3×) the yield derived from the sulfuric acid catalysis (~20-25%).

Alternatively, Scheme 3 shows a comparative schematic of dehydration cyclization of mannitol using, respectively, 1) 0.1-1 mol. % p-TsOH, 170° C., 1-2 h, and 2) 5 mol. % $H_3PO_3$, 170° C., 1-2 h. The isomannide yield for the p-toluenesulfonic (p-TsOH) catalyzed reaction is about 20-28%, with 60-72% product accountability, and having a dark drown, muddy color. The isomannide yield for the $H_3PO_3$ mediated reaction is comparable at about 23-41%, but the product accountability is greater, 73-82%, and the mixture shows lighter reddish to orange transparent appearance.

Table 3 summarizes some results for mannitol dehydrative cyclization using the two kinds of acid catalysts under different conditions.

TABLE 3

| Ex | Catalyst | Catalyst Load (mol %) | Time (min) | Temp (° C.) | Remaining Mannitol (wt. %) | Isomannide (wt. %) | 3,6-Sorbitan (wt. %) | Accountability (wt. %) | Color |
|---|---|---|---|---|---|---|---|---|---|
| 1 | $H_3PO_3$ | 5 | 180 | 160 | 0 | 23.24 | 55.95 | 81.69 | Red/orange, transparent |
| 2 | $H_3PO_3$ | 5 | 180 | 170 | 0 | 29.92 | 46.22 | 80.64 | Red/orange, transparent |
| 3 | $H_3PO_3$ | 5 | 320 | 170 | 0 | 34.38 | 39.81 | 76.69 | Red/brown, transparent |
| 4 | $H_3PO_3$ | 10 | 180 | 170 | 0 | 41.16 | 32.26 | 73.42 | Red/brown, transparent |
| 5 | p-TsOH | 1 | 60 | 170 | 0 | 25.96 | 41.89 | 68.45 | Dark brown, muddy |
| 6 | p-TsOH | 1 | 120 | 170 | 0 | 47.82 | 11.72 | 60.03 | Black, muddy |
| 7 | p-TsOH | 0.5 | 60 | 170 | 0 | 22.95 | 47.66 | 70.61 | Dark brown, muddy |
| 8 | p-TsOH | 0.5 | 120 | 170 | 0 | 38.74 | 23.97 | 62.71 | Black, muddy |
| 9 | p-TsOH | 0.1 | 60 | 170 | 0 | 19.36 | 52.82 | 72.18 | Dark brown, muddy |
| 10 | p-TsOH | 0.1 | 120 | 170 | 0 | 29.03 | 35.19 | 64.22 | Black, muddy |

The weak Brønsted acid, phosphonic acid, produces isomannide yields commensurate with the strong Brønsted acid, p-toluenesulfonic acid. Further, phosphonic acid shows a significantly greater product accountability and reduction in color bodies in the product mixture than p-toluenesulfonic acid.

C. —1,2,5,6-Hexanetetrol (HTO)

In another aspect, the present disclosure also describes a process for making a furanic-dehydration product in a similar manner as the process described above. In particular, the process involves dehydrative cyclization of 1,2,5,6-hexanetetrol (HTO) to rac-THF-diols.

In a further embodiment, one can employ phosphonic acid in an acid-mediated cyclization of 1,2,5,6-hexanetetrol (HTO) to THF-diols, such as described in Int'l. Appl. No.: PCT/US2014/33580, "Synthesis of R-Glucosides, Sugar alcohols, Reduced Sugar Alcohols, and Furan Derivatives of Reduced Sugar Alcohols," the content of which is incorporated herein by reference. Also derived from sorbitol hydrogenolysis, 1,2,5,6-HTO is an alternate polyol starting material for making THF-diols through ring closing.

Figure 11:
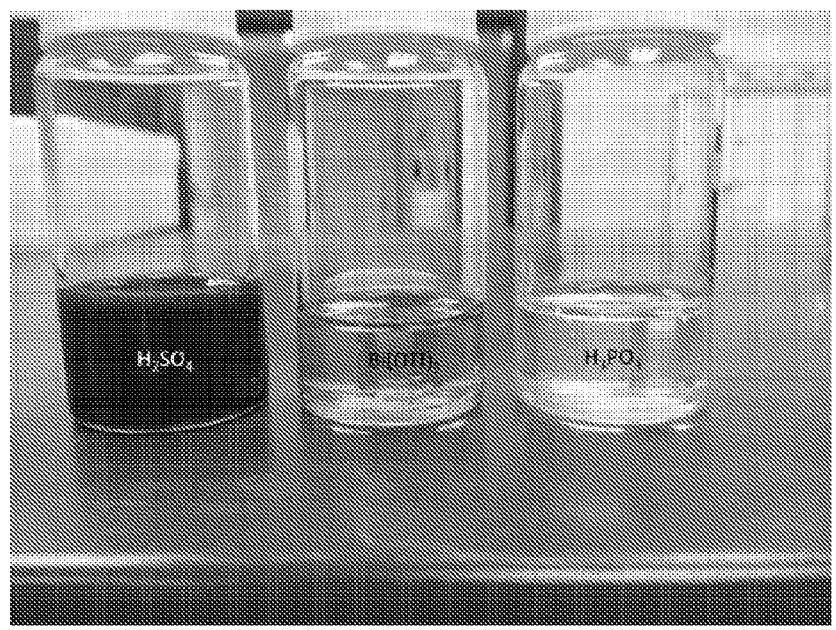
FIG. 11 is a photograph of three bottles containing samples of product of dehydration reactions converting sorbitol to isosorbide. From left to right, the catalyst used: A) 0.1 mol. % $H_2SO_4$; B) 0.1 mol. % $Bi(OTf)_3$; and C) 5 mol. % $H_3PO_3$. The photo shows pronounced product color retrenchment for the sample prepared using phosphonic acid vis-à-vis the other two samples.

FIG. 11 is a photo that compares three samples of THF-diols prepared from 1,2,5,6-HTO. From left to right, the samples are prepared using sulfuric acid, a conventional catalyst, a bismuth trifluoromethanesulfonate (triflate), a Lewis acid, and phosphonic acid. One observes a dramatic degree of color mitigation in the sample made using the phosphonic acid vis-à-vis the bismuth triflate, or the sulfuric acid. The phosphonic acid catalyzed sample is clear or near water-white (i.e., transparent and nearly or wholly colorless like clean water), whereas the Lewis acid sample, in the middle, is translucent but still quite yellowish, and sulfuric acid sample is opaque and brown-black in color.

D. —1,4-Anhydroxylitol

In another embodiment, phosphonic acid catalyst can likewise contribute to dehydration reactions for the preparation of 1,4-anhydroxylitol from xylitol with similar results from phosphonic acid catalyzed dehydration of sorbitol/mannitol to isohexides (i.e., improved accountability and color body retrenchment). To induce the dehydrative cyclization of xylitol, the reaction is conducted at least 130° C., and under a vacuum of at least 100 torr. Employ of a strong Brønsted or Lewis acid (e.g., sulfuric, sulfonic acid, Lewis acids) catalyst produces high conversion and copacetic yields of 1,4-anhydroxylitol; however, with concurrent production of considerable amounts of polymers or byproducts as observed in the product color. When phosphonic acid is used to cyclize dehydratively xylitol, the acid strength is adequate to induce the cyclization, but insufficient to effectuate polymerization and the production of significant amounts of side products. Further, phosphonic acid exhibits significantly elevated yields and product accountability. Scheme 3 outlines the acid-catalyzed dehydrative cyclization of mannitol to isomannide using the common Brønsted acid, $H_2SO_4$, and reducing Brønsted acid, $H_3PO_3$.

Figure 12:
FIG. 12 is a photograph of two bottles comparing samples containing product of dehydration reactions of xylitol to 1,4-anhydroxylitol prepared with p-TsOH (dark opaque color (left)) and with 10 mol % $H_3PO_3$, 120° C., 3 h. (light/clear transparent (right)).

In the photo of FIG. 12, we compare the results of xylitol dehydration performed using two different catalysts. In each sample, about 100 g. of xylitol is reacted according to the equation shown in Scheme 4.

Scheme 4.

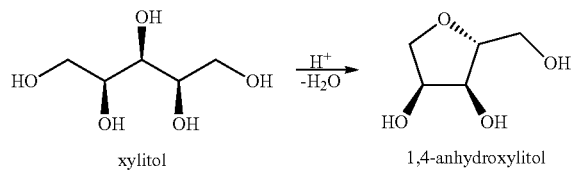

xylitol          1,4-anhydroxylitol

The first reaction used 1 mol. % p-TsOH, a conventional catalyst, at 140° C., for 1 h, at 75 torr. The second reaction used 5 mol. % $H_3PO_3$, at 150° C., for 1 h, at 75 torr. The xylitol in each reaction is converted completely (100%) for a yield of ~92 mol. % 1,4-anhydroxylitol. The reaction with p-TsOH catalyst generates an opaque, dark colored product sample (left); while in contrast, the reaction with $H_3PO_3$, catalyst makes a transparent, light colored (nearly water-white) product (right).

II. Examples

The following examples illustrate the preparation of cyclic dehydration products from some representative 5 or 6 carbon polyols according to the present invention, and associated advantageous properties for mitigating color and improving compositional accountability of the product mixtures.

Example 1: Dehydration of Sorbitol to Isosorbide Mediated by Phosphonic Acid or Sulfuric Acid

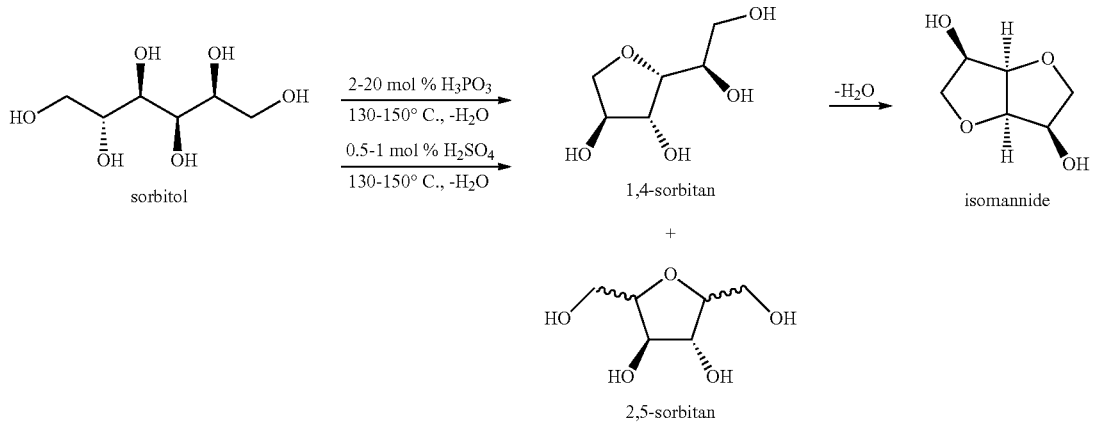 [SMILES: OC[C@@H](O)[C@@H](O)[C@H](O)[C@@H](O)CO ; OC[C@@H](O)[C@H]1OC[C@H](O)[C@H]1O ; "-H2O" ; O[C@@H]1CO[C@H]2[C@@H]1OC[C@H]2O ; OCC1OC(CO)[C@H](O)[C@H]1O]

General sorbitol dehydration procedure: A 500 mL, three neck round bottomed flask equipped with a PTFE coated magnetic stir bar was charged with 200 g of sorbitol (1.10 mol) and 2-20 mol % of phosphonic acid. The necks of the flask were fitted as follows: Short path condenser affixed to a 100 mL glass bulb receiver on the left, sleeved thermowell adapter threaded with a thermocouple on the central, and ground glass stopper on the right. The mixture was heated to temperatures between 130 and 150° C., under a vacuum between 5 and 10 torr for 1-3 hours. Upon completion, the product matrix was cooled, vacuum broken, and weights of products and water (bulb receiver) measured. Analysis was carried out by gas chromatography employing a derivitization method (—OH acetylation).

Example 2: Dehydration of Mannitol to Isomannide Mediated by Phosphonic Acid or Sulfuric Acid

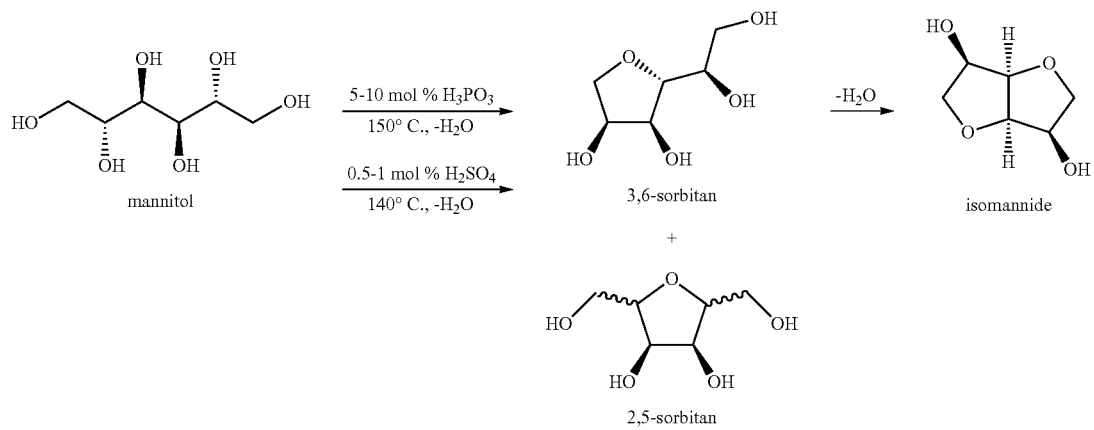 [SMILES: OC[C@@H](O)[C@@H](O)[C@H](O)[C@H](O)CO ; OC[C@@H](O)[C@H]1OC[C@H](O)[C@@H]1O ; "-H2O" ; O[C@@H]1CO[C@H]2[C@@H]1OC[C@H]2O ; OCC1OC(CO)[C@H](O)[C@@H]1O]

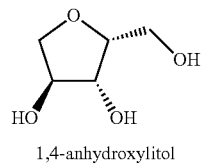

1,4-anhydroxylitol

Experimental: A 250 mL, three neck round bottomed flask equipped with a PTFE coated magnetic stir bar was charged with 100 g of sorbitol (0.657 mol) and 5% of phosphonic acid or 1 mol % p-toluenesulfonic acid. The necks of the flask were fitted as follows: Short path condenser affixed to a 100 mL glass bulb receiver on the left, sleeved thermowell adapter threaded with a thermocouple on the central, and ground glass stopper on the right. The phosphonic acid mixture was heated to a temperature of 150° C. and the p-toluenesulfonic acid mixture heated to 140° C., under a vacuum between 5 and 10 torr for 1 hour. Upon completion, the product matrix was cooled, vacuum broken, and weights of products and water (bulb receiver) measured. Analysis was carried out by gas chromatography employing a derivitization (—OH acetylation) method, which disclosed an approximately 91% mol yield of 1,4-anhydroxylitol in each product mixture.

Example 4: Dehydration of 1,2,5,6-Hexanetetrol (HTO) to Rac-bHMTHFs

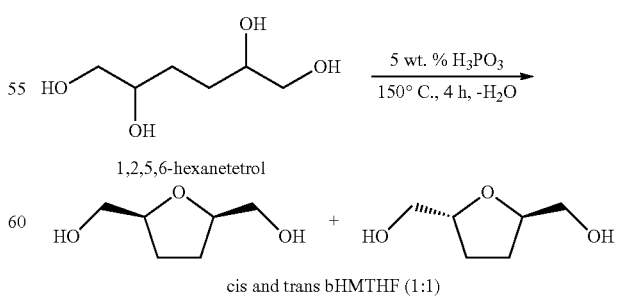

Experimental: A three neck, 500 mL round bottomed flask equipped with a PTFE coated magnetic stir bar was charged with 300 g of a mesophasic, off-white oil comprised of ~42

General mannitol dehydration procedure: A 500 mL, three neck round bottomed flask equipped with a PTFE coated magnetic stir bar was charged with 200 g of morbitol (1.10 mol) and 5-10 mol % of phosphonic acid. The necks of the flask were fitted as follows: Short path condenser affixed to a 100 mL glass bulb receiver on the left, sleeved thermowell adapter threaded with a thermocouple on the central, and ground glass stopper on the right. The mixture was heated to 150° C., under a vacuum between 5 and 10 torr for 2-3 hours. Upon completion, the product matrix was cooled, vacuum broken, and weights of products and water (bulb receiver) measured. Analysis was carried out by gas chromatography employing a sample derivitization (—OH acetylation) method.

Example 3: Dehydration of Xylitol to 1,4-Anhydroxylitol Mediated by Phosphonic Acid or p-Toluenesulfonic Acid

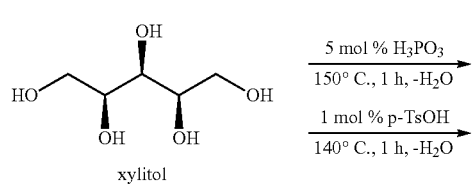

wt. % 1,2,5,6-hexanetetrol (HTO), and 3.44 g of phosphonic acid ($H_3PO_3$, 5 mol % relative to HTO). One neck was capped with a ground glass joint, the center with a sleeved thermowell adapter fitted with a thermocouple, and the last a short path condenser affixed to a dry-ice cooled 250 mL pear-shaped receiver. While vigorously stirring, the mixture was heated to 150° C. under vacuum (20 torr) for 4 hours. After this time, the vacuum was broken and residual, light colored oil cooled, and weighed, furnishing 3.06 g. GC analysis conferred that 95 mol % of the HTO had converted to bHMTHF with a 88% mol yield.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently know or to be developed, which may be used within the scope of the invention. Therefore, unless changes otherwise depart from the scope of the invention, the changes should be construed as being included herein.

We claim:

1. A method for preparing isosorbide from sorbitol, comprising: dehydrating sorbitol with a phosphonic acid catalyst at elevated temperatures to produce a product mixture including isosorbide and sorbitans, then recovering isosorbide from the product mixture.

2. The method according to claim 1, wherein isosorbide is recovered from the product mixture by at least a means selected from the group consisting of chromatography, crystallization, and distillation.

3. The method according to claim 1, wherein said phosphonic acid is present at a catalyst load of about 1 mol. % to about 20 mol. % relative to a concentration of sorbitol.

4. The method according to claim 3, wherein said phosphonic acid is at a catalyst load of about 2 mol. % to about 15 mol. % relative to a concentration of sorbitol.

5. The method according to claim 1, wherein said reaction temperature is in a range from about 100° C. up to about 160° C.

6. The method according to claim 1, wherein is produced as the primary product and 1,4-sorbitan is the next most favored product.

7. The method according to claim 1, wherein said the reaction time is up to about 3 hours.

8. The method according to claim 1, wherein said reaction is at an operating pressure of about 5 torr to about 100 torr.

9. The method according to claim 1, wherein said reaction is at an operating pressure of about 10 torr to about 30 torr.

* * * * *